US00PP36637P3

(12) United States Plant Patent
Korlipara

(10) Patent No.: US PP36,637 P3
(45) Date of Patent: Apr. 29, 2025

(54) ***AGASTACHE* PLANT NAMED 'Pink Pearl'**

(50) Latin Name: ***Agastache* hybrid**
Varietal Denomination: Pink Pearl

(71) Applicant: Terra Nova Nurseries, Inc., Canby, OR (US)

(72) Inventor: Harini Korlipara, Tualatin, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 59 days.

(21) Appl. No.: 18/128,812

(22) Filed: Mar. 30, 2023

(65) Prior Publication Data

US 2024/0334860 P1 Oct. 3, 2024

(51) Int. Cl.

| | |
|---|---|
| ***A01H 5/02*** | (2018.01) |
| ***A01H 5/10*** | (2018.01) |
| ***A01H 6/50*** | (2018.01) |

(52) U.S. Cl.
USPC ..... Plt./399
CPC ..... *A01H 6/50* (2018.05); *A01H 5/10* (2013.01)

(58) Field of Classification Search
USPC ..... Plt./399
CPC ..... A01H 5/02; A01H 5/00; A01H 6/50
See application file for complete search history.

(56) References Cited

U.S. PATENT DOCUMENTS

PP25,613 P3 * 6/2015 Egger ..... A01H 5/02 Plt./399

* cited by examiner

*Primary Examiner* — June Hwu
(74) *Attorney, Agent, or Firm* — The Webb Law Firm

(57) ABSTRACT

A new and distinct *Agastache* plant characterized by pink flowers in large inflorescences, a long bloom time, a very dense, medium compact habit, good winter hardiness, and very high vigor.

2 Drawing Sheets

Botanical classification: *Agastache* hybrid.
Varietal denomination: 'Pink Pearl'.

BACKGROUND OF THE NEW PLANT

The present invention comprises a new and distinct *Agastache* plant, of the family Lamiaceae, having the varietal name 'Pink Pearl'. This new variety is one of several selections of new *Agastache* using hardy and dwarf *Agastache* species in the breeding lines to provide hardiness and compactness. 'Pink Pearl' is a selection from a cross of unpatented, proprietary seedlings *Agastache* 76-2, as the seed parent, and *Agastache* 64-3, as the pollen parent, in Canby, Oregon. 'Pink Pearl' was selected for its compact habit, hardiness, and pink flowers in large, dense heads.

When compared to its seed parent, the new variety is larger and hardier with pink flowers rather than coral-orange flowers. When compared to its pollen parent, the new variety is shorter and exhibits better branching. When compared to *Agastache* plant named 'Kudos Coral' (U.S. Plant Pat. No. 25,613), the new variety is larger and exhibits better branching.

The new variety has only been reproduced by asexual propagation (cuttings and micropropagation). Each of the progeny exhibits identical characteristics to the original plant. Asexual propagation by stem cuttings and micropropagation using apical buds and nodes performed in Canby, Oregon shows that the characteristics and distinctions described herein come true to form and are established and transmitted through succeeding propagations. The present invention has not been evaluated under all possible environmental conditions. The phenotype may vary with variations in environment without a change in the genotype of the plant.

When compared to other *Agastache* plants known to the breeder, the new variety is characterized by the following:

1. Bright pink flowers on numerous inflorescences;
2. Long bloom time;
3. A medium, compact habit;
4. Good winter hardiness; and
5. Very high vigor, growth rate of approximately 60 cm per year.

DESCRIPTION OF THE DRAWINGS

The accompanying photographic drawings illustrate the new variety, with the colors being as nearly true as possible with color illustrations of this type.

DETAILED BOTANICAL DESCRIPTION

Figure 1:
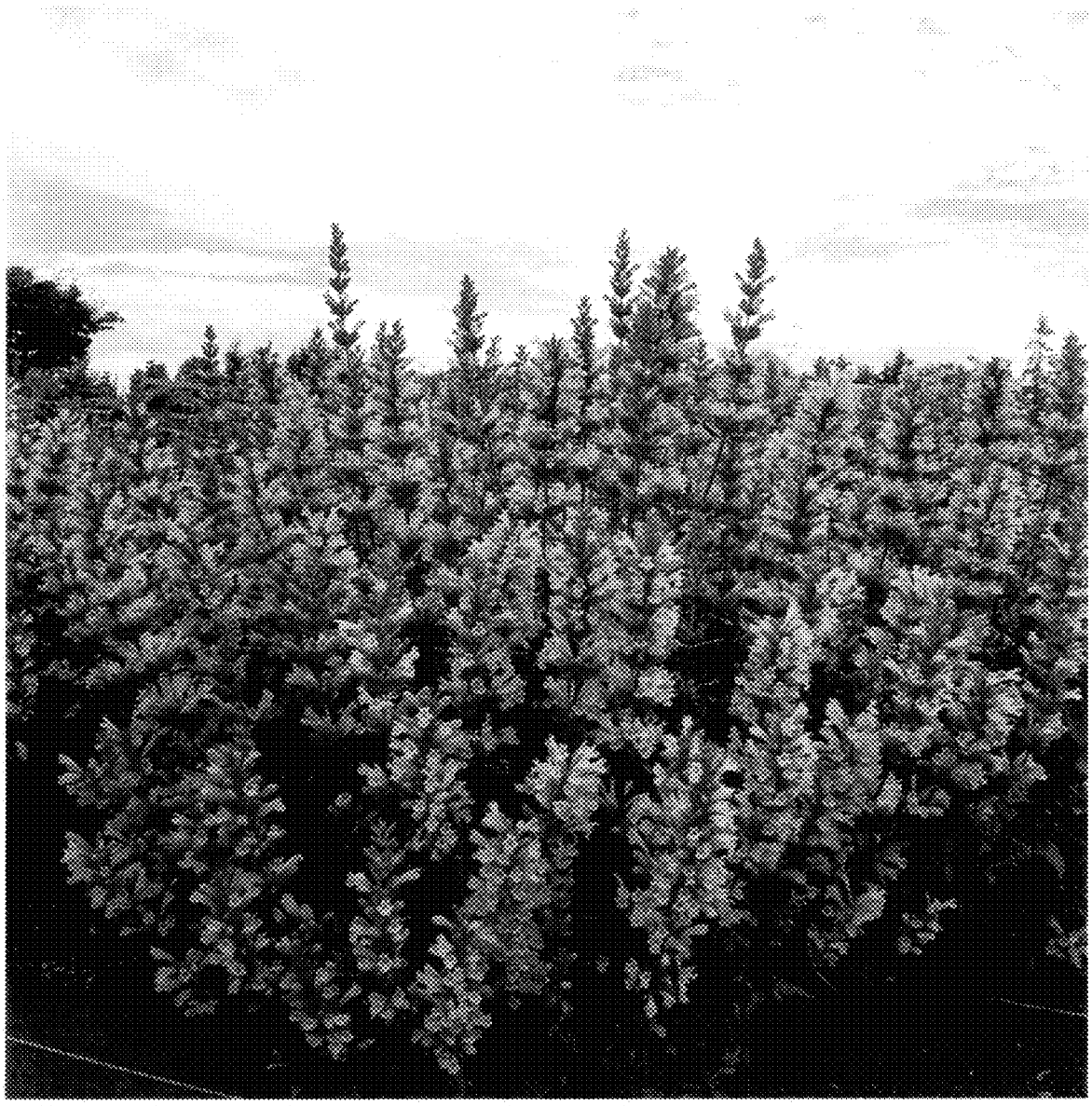
FIG. 1 illustrates a 9-month-old plant of the new variety growing in a field in mid-summer in Canby, Oregon.
Figure 2:
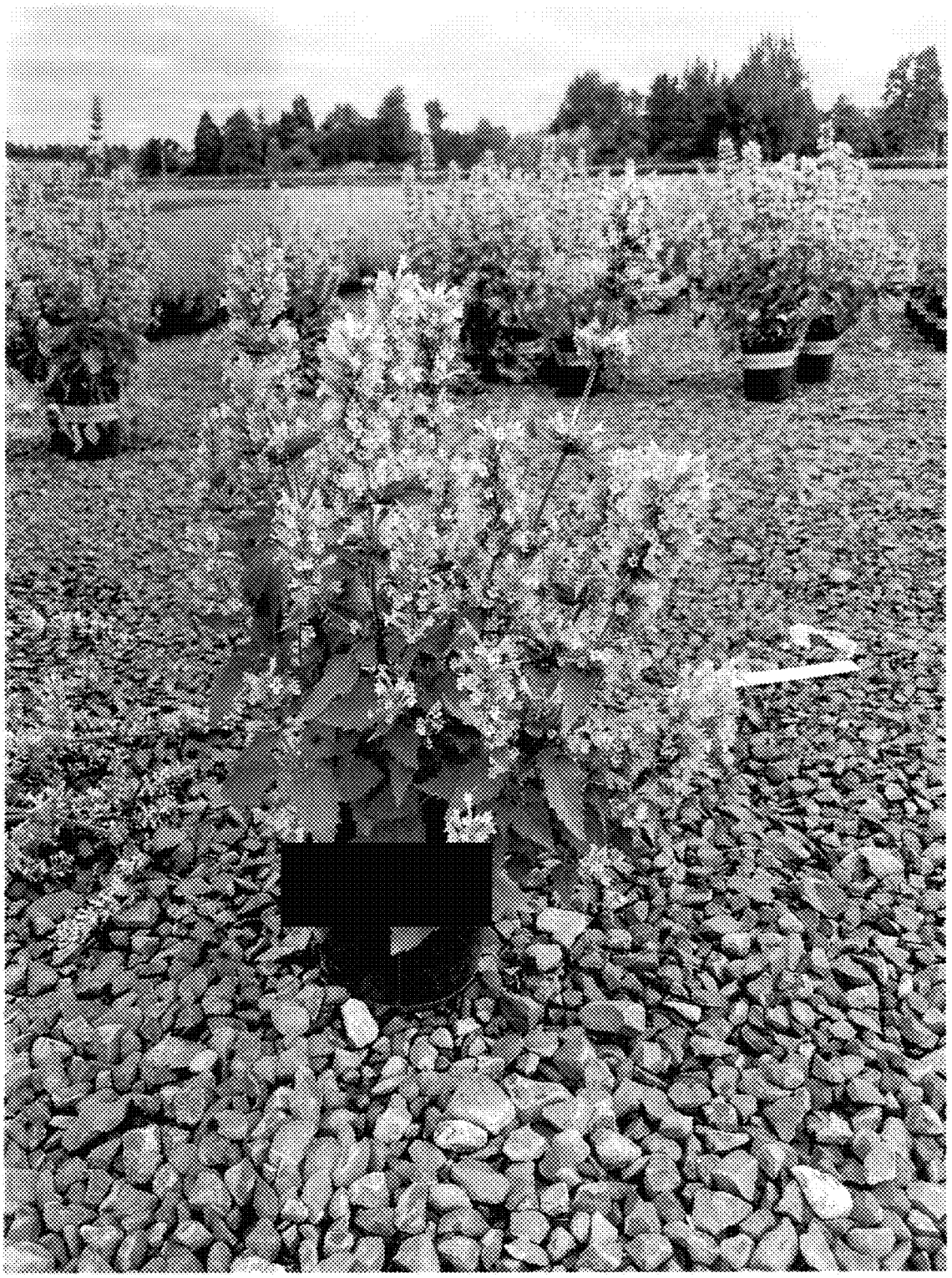
FIG. 2 illustrates a young plant of the new variety grown in a 1 gallon container in full sun in Yamhill, Oregon.

The following is a detailed description of the new variety based on observations of 4-month-old plants in late May grown outside in full sun in 1 gallon containers in Canby, Oregon (USDA Zone 8). Temperatures range from a high of 35° C. in August to a low of 0° C. in January. Normal rainfall in Canby, Oregon is around 1 m per year. Color references are based on The 2007 R.H.S. Colour Chart of The Royal Horticultural Society of London, $5^{th}$ Edition.

Plant:

*Type*.—Herbaceous perennial.

*Hardiness*.—USDA Zones 6 to 10.

*Size*.—45.0 cm wide and 42.0 cm tall to the top of the flowers.

*Form*.—Upright.

*Vigor*.—Very high, growth rate of approximately 60 cm per year.

*Branching*.—About 8 main stems from the base that branch at every node.

*Stem*.—Shape: Square in cross section. Length: To 22.0 cm to the first flower. Width: 4.0 mm at the base. Texture: Pubescent. Internode length: From 2.0 to 7.0 cm. Color: RHS N137B.

*Roots*.—RHS 155B; fibrous; plants root easily from stem tip cuttings.

Foliage:

*Type*.—Simple.

*Leaf arrangement*.—Opposite.

*Shape*.—Ovate.

*Length*.—To 32.0 mm.

*Width*.—To 35.0 mm.

*Margin*.—Crenate.

*Apex*.—Acute.

*Base*.—Truncate to cordate.

*Leaf texture* (*both surfaces*).—Pubescent.

*Upper surface color*.—RHS N138B, including the venation.

*Lower surface color*.—Closest to RHS 138C, with the venation being RHS 138B.

*Venation*.—Pinnate.

*Fragrance*.—Aromatic.

*Petiole*.—Length: 28.0 mm. Width: 1.0 mm. Texture: Pubescent. Color: RHS N137B.

Flowers:

*Bud*.—Length: 25.0 mm. Width: 7.0 mm at the widest point prior to opening. Shape: Tubular. Texture: Pubescent. Color: RHS 47C.

*Type*.—Zygomorphic.

*Shape*.—Tubular, bilabiate.

*Flower size*.—To 32.0 mm long and 8.0 mm wide.

*Inflorescence type*.—Terminal spike with up to 15 whorls.

*Flower number per inflorescence*.—About 180.

*Inflorescence size*.—To 20.0 cm long and 6.0 cm wide.

*Bloom period*.—June through frost in Canby, Oregon.

*Lastingness*.—Spikes last about 4 weeks on the plant, flowers last about 7-10 days.

*Fragrance*.—Aromatic.

*Peduncle*.—Length: 5.0 cm. Width: 2.0 mm. Texture: Pubescent. Color: RHS 137B.

*Pedicel*.—Length: 2.0 mm. Texture: Pubescent. Color: RHS N186C.

*Corolla*.—Length: 32.0 mm. Width: 8.0 mm. Description: Tube measures 27.0 mm long and from 1.0 to 4.0 mm wide, flaring into 5 lobes. The inner and outer surfaces are RHS 47C. The inner surface is glabrous and the outer surface is pubescent. The two top, joined lobes are oblong in shape, have obtuse tips, and entire margins (measuring 3.0 mm long and 5.0 mm wide). Two of the three lower lobes spread sideways and are reflexed, have acute tips, and entire margins (measuring 3.0 mm long and 3.0 mm wide). The final lower lobe is cupped, broadly ovate, notched at the tip, and has a serrate margin (measuring 5.0 mm wide and 4.0 mm deep).

*Calyx*.—Shape: Campanulate. Arrangement: 5 lobes that are ovate in shape and 1.5 mm long. Size: 7.0 mm long and 2.0 mm wide. Apex: Acuminate. Margin: Entire. Texture: Pubescent outer surface and glabrous inner surface. Color: Outer surface of RHS 187A and inner surface of RHS 71A.

*Pistil*.—1; 33.0 mm long.

*Ovary*.—1.0 mm long; RHS 145C.

*Style*.—28.0 mm long; RHS NN155C at the bottom, blending to RHS 70A at the top.

*Stigma*.—Two-parted; 1.0 mm deep; RHS N77B.

*Stamen*.—4, paired and exerted; top two are 10.0 mm long; bottom two are 7.0 mm long.

*Filament*.—RHS 72C.

*Anther*.—1.0 mm long; RHS 75C.

*Pollen*.—RHS NN155D.

Fruit/seed:

*Number*.—4 nutlets.

*Shape*.—Ovoid.

*Size*.—1.0 mm long.

*Color*.—RHS 202A.

Pests/diseases: No unusual resistance or susceptibility noted to date.

I claim:

1. A new and distinct variety of *Agastache* plant named 'Pink Pearl', substantially as illustrated and described herein.

* * * * *